United States Patent [19]

Nielsen et al.

[11] Patent Number: 4,636,211
[45] Date of Patent: Jan. 13, 1987

[54] BIFOCAL INTRA-OCULAR LENS

[76] Inventors: J. McHenry Nielsen, 2339 Sunset Point Rd., Clearwater, Fla. 33575; Wayne G. Miller, 6375 Lane Rd., Sarasota, Fla. 33580

[21] Appl. No.: 588,926
[22] Filed: Mar. 13, 1984
[51] Int. Cl.[4] .............................................. A61F 2/16
[52] U.S. Cl. ...................................... 623/6; 351/161; 351/168
[58] Field of Search .................. 3/13; 623/6; 351/161, 351/168

[56] References Cited

U.S. PATENT DOCUMENTS

| 3,555,126 | 1/1971 | Gitson | 351/168 X |
| 3,726,587 | 4/1973 | Kendall | 351/161 |
| 4,206,518 | 1/1980 | Jardon et al. | 3/13 |
| 4,316,293 | 2/1982 | Bayers | 3/13 |
| 4,402,579 | 9/1983 | Poler | 3/13 |
| 4,435,856 | 3/1984 | L'Esperance | 3/13 |

OTHER PUBLICATIONS

"Ultrafocal Bifocal Contact Lens" by Claud A. Kendall, Contacto, Jan. 1976, pp. 31-35.

Primary Examiner—Ronald L. Frinks
Attorney, Agent, or Firm—James C. Wray

[57] ABSTRACT

An intra-ocular lens consisting of a transparent body has concentrically oriented near vision and far vision, optically powered portions with the near vision portion being centrally positioned relative to the body and the far vision portion being coaxial with and surrounding the near vision portion, the lens being fixed in a position such that the near vision portion is aligned with the pupillary aperture of the eye and is fixed in alignment.

1 Claim, 5 Drawing Figures

BIFOCAL INTRA-OCULAR LENS

BACKGROUND OF THE INVENTION

This invention relates generally to post-cataract patient care and vision improvement and, more particularly, to an intra-ocular bifocal lens implantable in a human eye to replace the natural lens, having been removed, for instance, in a cataract operation. Commonly, thick glasses have been used for correcting the vision of post-cataract patients. However, the glasses have obvious disadvantages associated with the size and weight of the glasses. The present invention circumvents the need for heavy glasses by creating a pseudophakia or an eye in which a plastic lenticulus is substituted for the extracted cataract.

The concept of creating a concentric bifocal lens has been shown for contact lenses. U.S. Pat. No. 3,726,587 is an example. Contact lenses have a converging meniscus shape in order to conform to the rounded shape of the cornea. Such a shape could not apply in an intra-ocular implantation. Other types of multiple focus contact lenses are well known. U.S. Pat. No. 3,794,414 shows a lens having a light-transmitting area interrupted by spaced-apart, opaque portions. U.S. Pat. No. 3,962,505 shows a nearly concentric portion of a contact lens for bifocal vision.

Most of the prior art related to intra-ocular lenses deals with fixation means for securing the lens in either the posterior or anterior chamber of the eye. U.S. Pat. No. 4,010,496 shows an intra-ocular lens having upper and lower refractive segments for near and far vision.

SUMMARY OF THE INVENTION

Pseudophakic eyes generally are such that the pupils rarely exceed 4 mm in diameter in photopic conditions, nor do the pupils generally constrict to less than 2 mm in diameter. It is also well known that slight pupillary constriction occurs when the eye attempts to focus at near vision. The eye functions not only as a seeing mechanism but, also, as a light collecting mechanism. At any given pupil diameter, light enters the eye and is focused on the retina. By changing the path of a portion of the light, it is possible to achieve bi-vision. For example, if a 3 mm pupil in 80 foot candles of illumination (approximately that found in modern offices) is juxtaposed to a centrally placed 2.12 mm diameter optic powered for near, the optic being surrounded concentrically by a far vision optic, multiple focus can be achieved. In the example, one half of the pupillary area is powered for near vision while the balance is powered for far vision.

Focusing at near the central lens portion puts the image on the retina, and mild pupillary constriction aids in focusing. Although pupillary constriction is helpful, it is not necessary for the concentric lens. When the eye looks up to far objects, the near focal power is automatically out of focus while the concentric distant power takes over to provide clarity for the far vision. This occurs because of the large light collecting area of the concentric distant portion of the lens. Even when extremely bright objects at a distance stimulate increased pupillary constriction, the increase in depth of focus counters any blurring from the centrally located near optic.

Should sunglasses be used to eliminate irritating brightness in far vision so that the pupil relaxes, the light collected by the concentric distance lens portion increases to offset the reduction in depth of focus. Hence, sharp far vision occurs even in diminished light.

Since the difference in the effective power between far and near vision is approximately +2.50 diopters in the average aphapic patient, sufficient distinction in focus is realized to provide rapid neuro-transfer of far to near vision. This phenomenon, plus the appropriate light collecting area for a given pupil area, provides the efficacy of the present intra-ocular optic design. To maintain the effectiveness of the design, the range of powers in the far vision portion of the lens is limited to a range of from +10.00 diopters to +30.00 diopters effective power, while the near optic power range is limited to from +10.00 diopters to +40.00 diopters effective power.

While lens diameter may vary with need, 6 mm is average. The central near optic can vary in diameter relative to need, but 2.12 mm is average for a 3.0 mm pupil stimulated by approximately 80 foot candles of illumination.

The lens can have a plano-convex or bi-convex shape and can be fabricated by lathe cutting, compression or injection molding or electro-forming. The near optic may be placed on either surface with the power corrected accordingly.

An object of the invention is, therefore, to provide an intra-ocular bifocal lens for post-cataract patients which eliminates the need for heavy, uncomfortable glasses.

Another object of the invention is to provide the post-cataract patient with an intra-ocular bifocal lens which enables the patient to achieve both near and far vision with clarity.

Another object of the invention is to provide an intra-ocular lens of one-piece construction.

Still another object of the invention is to provide simultaneous vision for near and far in the absence of the natural crystalline lens.

DETAILED DESCRIPTION OF THE INVENTION

Figure 1:
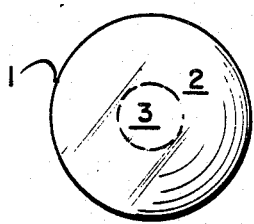
FIG. 1 is a plane view of the intra-ocular bifocal lens.
Figure 2:
FIG. 2 shows a sectional view of the intra-ocular lens having a plano-convex shape.
Figure 3:
FIG. 3 is a sectional view of the intra-ocular bifocal lens having a bi-convex shape.

Referring to FIG. 1, the intra-ocular bifocal lens is indicated generally by the number 1. The one-piece body has a centrally located optically powered portion for near vision, designated as number 3, which is surrounded by a far vision optically powered portion 2, the two portions being concentric and coaxial. While the body is divided into two distinct portions, each portion being optically powered, the body itself has a one-piece construction. The body, in cross section, can be either plano-convex, as shown in FIG. 2, or bi-convex, as shown in FIG. 3.

After a cataract operation in which a natural crystalline lens is removed from a human eye, the intra-ocular bifocal lens can be implanted in either the anterior or posterior chamber of the eye.

Figure 4:
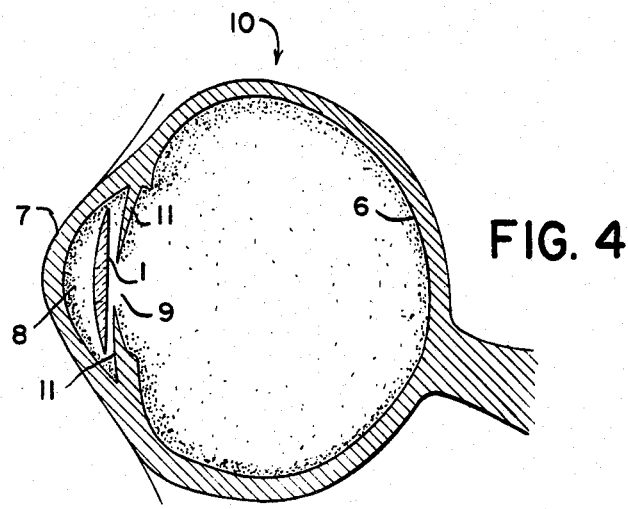
FIG. 4 shows a sectional view of a human eye with the intra-ocular bifocal lens implanted in the anterior chamber.
Figure 5:
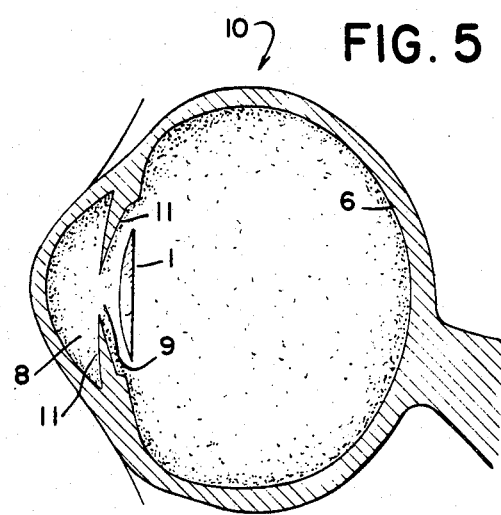
FIG. 5 shows a sectional view of a human eye with the intra-ocular lens implanted in the posterior chamber.

FIG. 4 shows a human eye with the lens implanted in the anterior chamber, while FIG. 5 shows implantation in the posterior chamber. In either chamber, the lens is fixed in place. It can be done so using a variety of methods. Multiple suspensory or fixation methods currently exist in a generic form that may be applied to the present invention.

Referring now to FIG. 4, the eye is shown generally by the reference numeral 10. The anterior chamber 8 is defined by the interior wall of the cornea 7 and iris 11. The pupillary aperture 9 extends from the anterior chamber 8 to the posterior chamber 9. The retina is shown generally as number 6. The central portion or near vision portion of the lens is axially aligned with the pupillary aperture 9. The central portion is aligned with the pupillary aperture when the lens is positioned in the posterior chamber, as shown in FIG. 5. Under normal lighting conditions, the pupillary aperture 9 has a diameter slightly larger than the central near vision portion of the lens. In either FIGS. 4 or 5, light passes through the pupillary aperture 9 and is focused on the retina 6. By changing the path of a portion of that light, the concentric bifocal intra-ocular lens will create bi-vision. Optimally, if the pupillary aperture is 3 mm in diameter, a bifocal intra-ocular lens will have a central near vision portion having a 2.12 mm diameter. Half of the pupillary area will be powered for near vision while the other half will be powered for far vision.

Focusing at near the central portion puts the image on the retina 6. Some pupillary constriction may clarify the image, but it is not required. When the eye 10 looks up to far objects, the near vision portion is automatically out of focus while the far vision portion becomes effective to provide clarity for far vision. This occurs because of the large light collecting area of the far vision portion of the lens.

Embodiments shown and described herein provide examples of the invention with the understanding that modifications may be made.

What we claim is:

1. An intra-ocular lens adapted to be implanted in a human eye comprising a transparent single one-piece lens body, the transparent body having a permanently fixed centrally located, near vision optically powered first portion and a concentrically located, far vision optically powered second portion, the first portion having an average diameter of approximately 2.12 mm and the body having an average diameter of approximately 6 mm, the first portion being optically powered within the range of from +10.00 to +30.00 diopters effective power and the second portion being optically powered within the range of from +10.00 to +30.00 diopters effective power, the difference in effective power between the first and second portions averaging +2.50 diopters effective power in order to ensure distinction in focus and to provide rapid neuro-transfer between near and far vision.

* * * * *